United States Patent
Armstrong

(10) Patent No.: US 9,770,559 B2
(45) Date of Patent: Sep. 26, 2017

(54) SYRINGE WITH CLICKING MECHANISM

(71) Applicant: Sean Terrence Armstrong, Bedfordview (ZA)

(72) Inventor: Sean Terrence Armstrong, Bedfordview (ZA)

( * ) Notice: Subject to any disclaimer, the term of this patent is extended or adjusted under 35 U.S.C. 154(b) by 6 days.

(21) Appl. No.: 14/761,814

(22) PCT Filed: Jan. 22, 2014

(86) PCT No.: PCT/ZA2014/000002
§ 371 (c)(1),
(2) Date: Jul. 17, 2015

(87) PCT Pub. No.: WO2014/121307
PCT Pub. Date: Aug. 7, 2014

(65) Prior Publication Data
US 2015/0359969 A1 Dec. 17, 2015

(30) Foreign Application Priority Data

Jan. 30, 2013 (ZA) .................. 2013/00770
May 22, 2013 (ZA) .................. 2013/03714

(51) Int. Cl.
*A61M 5/315* (2006.01)
*A61M 5/31* (2006.01)

(52) U.S. Cl.
CPC ...... *A61M 5/31526* (2013.01); *A61M 5/3134* (2013.01); *A61M 5/3158* (2013.01);
(Continued)

(58) Field of Classification Search
CPC ...... A61M 2005/5073; A61M 5/31555; A61M 2005/31516; A61M 5/31526;
(Continued)

(56) References Cited

U.S. PATENT DOCUMENTS 3,934,586 A  1/1976 Easton
3,938,505 A  2/1976 Jamshidi
(Continued)

FOREIGN PATENT DOCUMENTS

DE  807113  6/1951
WO  2008016381  2/2008
WO  2008057976  5/2008

OTHER PUBLICATIONS

Search Report and Written Opinion for Priority International Application serial No. PCT/ZA2014/000002 dated May 21, 2014.

*Primary Examiner* — Nathan R Price
*Assistant Examiner* — John Doubrava
(74) *Attorney, Agent, or Firm* — Haugen Law Firm PLLP

(57) ABSTRACT

A syringe includes a monolithic barrel (12) being divided into two bore portions, a first bore portion (22) extending from the needle adapter partially towards the second axial end and a second bore portion (24) extending from the first bore portion to the second axial end, wherein the first bore portion is circular in cross section and the second bore portion has a cross sectional shape that at least partially extends beyond the radius of the first bore portion. The syringe includes a plunger (14) sized to fit within and move along the longitudinal axis of the first bore portion. A plunger rod (16) extends along the longitudinal axis of the monolithic barrel, the plunger rod including a first array of notches and/or protuberances (30) along at least a portion of its length. The syringe includes an insert (18) sized to fit wholly within the second bore portion, the insert defining a bore through which the plunger rod extends and including a first finger (36) extending into the bore defined by the insert for, in use, engaging the first array of notches and/or protuberances on the plunger.

10 Claims, 4 Drawing Sheets

(52) U.S. Cl.
CPC .... *A61M 5/31505* (2013.01); *A61M 5/31591* (2013.01); *A61M 5/31595* (2013.01); *A61M 2205/581* (2013.01)

(58) Field of Classification Search
CPC ............ A61M 5/3158; A61M 5/31591; A61M 2205/581; A61M 5/31595; A61M 5/3134
See application file for complete search history.

(56) References Cited

U.S. PATENT DOCUMENTS

| | | | |
|---|---|---|---|
| 4,642,102 A | 2/1987 | Ohmori | |
| RE33,821 E * | 2/1992 | Banks | A61M 5/5013 604/110 |
| 5,215,533 A * | 6/1993 | Robb | A61M 5/315 604/110 |
| 5,328,476 A * | 7/1994 | Bidwell | A61M 5/5013 604/110 |
| 5,380,295 A * | 1/1995 | Vacca | A61M 5/315 604/187 |
| 5,578,015 A * | 11/1996 | Robb | A61M 5/315 604/110 |
| 6,413,236 B1 * | 7/2002 | Van Dyke | A61M 5/3234 604/110 |
| 6,579,269 B1 * | 6/2003 | Kleyman | A61M 5/31555 604/207 |
| 8,052,654 B2 * | 11/2011 | Kaal | A61M 5/5013 604/209 |
| 8,137,324 B2 * | 3/2012 | Bobst | A61M 5/5013 604/110 |
| 8,277,422 B2 * | 10/2012 | Oliver | A61M 5/3234 604/110 |
| 2003/0212366 A1 * | 11/2003 | Bang | A61M 5/322 604/196 |
| 2006/0184136 A1 * | 8/2006 | Kleyman | A61M 5/31595 604/210 |
| 2007/0135764 A1 * | 6/2007 | Chen | A61M 5/322 604/110 |
| 2008/0281266 A1 * | 11/2008 | Walton | A61M 5/5013 604/110 |
| 2010/0076370 A1 * | 3/2010 | Howlett | A61M 5/1424 604/65 |
| 2011/0009829 A1 * | 1/2011 | Kosinski | A61M 5/31511 604/218 |
| 2012/0004607 A1 * | 1/2012 | Walton | A61M 5/322 604/110 |
| 2012/0022467 A1 * | 1/2012 | Shovary | A61M 5/31501 604/220 |
| 2012/0316509 A1 * | 12/2012 | Kayser | A61M 5/19 604/210 |
| 2014/0276592 A1 * | 9/2014 | Mottola | A61M 5/31505 604/506 |
| 2014/0288507 A1 * | 9/2014 | Samuel | A61M 5/31513 604/222 |

* cited by examiner

SYRINGE WITH CLICKING MECHANISM

BACKGROUND

The present invention relates to a syringe. More specifically, the present invention relates to a syringe that generates audible clicks as the plunger rod moves relative to the barrel.

Syringes with mechanisms for regulating or monitoring movement of a plunger along a barrel are known. For instance:

- U.S. Pat. No. 3,934,586 to Easton describes a syringe with tabs on the plunger rod that engage with wedges extending radially inwards from the barrel;
- DE807,113 describes a syringe with tabs extending from the plunger rod and a regulator attachable to the outer perimeter of the barrel to regulate relative movement of the plunger rod and barrel; and
- U.S. Pat. No. 4,642,102 to Ohmori describes a stopper secured to and incrementally movable along the plunger rod, which stopper limits relative movement of the plunger rod and barrel when the stopper comes into contact with the barrel.

It is an object of the present invention to provide an insert for a syringe that is separate from the barrel, that is sized to locate within the barrel, and that creates an audible sound when the plunger rod moves relative to the barrel.

SUMMARY OF THE INVENTION

According to a first embodiment of the present invention, a syringe includes:

- a monolithic barrel defining a longitudinal axis, first and second axial ends, and a bore extending along the longitudinal axis, the bore terminating in a needle adapter at the first axial end and being divided into two bore portions, a first bore portion extending from the needle adapter partially towards the second axial end and a second bore portion extending from the first bore portion to the second axial end, wherein the first bore portion is circular in cross section and the second bore portion has a cross sectional shape that at least partially extends beyond the radius of the first bore portion;
- at least one finger flange extending from the monolithic barrel;
- a plunger sized to fit within and move along the longitudinal axis of the first bore portion, with the plunger sealed against the inner wall of the monolithic barrel within the region of the first bore portion;
- a plunger rod extending along the longitudinal axis of the monolithic barrel towards the second axial end, the plunger rod including a first array of notches and/or protuberances along at least a portion of its length; and
- an insert sized to fit wholly within the second bore portion, the insert defining a bore through which the plunger rod extends and including a first finger extending into the bore defined by the insert for, in use, engaging the first array of notches and/or protuberances on the plunger rod.

Typically, the plunger rod includes a second array of notches and/or protuberances extending from a side of the plunger rod opposite the side on which the first array of notches and/or protuberances are located.

Generally, the insert includes a second finger arranged opposite the first finger, which second finger extends into the bore defined by the insert and, in use, engages the second array of notches and/or protuberances.

Preferably, the second bore portion has a diameter greater than the first bore portion and the first and second bore portions share a common longitudinal axis.

Typically, the first bore portion extends from the needle adapter to the at least one finger flange and the second bore portion extends from the first bore portion to the second axial end of the barrel.

Generally, the insert is right circular cylindrical with a diameter corresponding to the diameter of the second bore portion.

Preferably, the axial height of the insert substantially corresponds with the length of the second bore portion, such that the insert does not protrude from the second axial end of the barrel.

Typically, (i) the barrel in the region of the second bore portion includes at least one notch and/or protuberance on its inner radial surface and/or (ii) the insert includes at least one notch and/or protuberance on its outer radial surface to secure the insert within the second bore portion. Alternatively, the insert is adhered to the barrel within the second bore portion. Further alternatively, the insert is secured to the barrel within the second bore portion by an interference fit between the insert and barrel.

Generally, the insert includes third and fourth fingers, wherein the first, second, third and fourth fingers are symmetrically arranged around the bore defined by the insert.

Preferably, the plunger rod, in section orthogonal to its longitudinal axis, has a shape wherein four equally spaced arms of the same length radiate radially from the longitudinal axis.

Typically, the first array of notches and/or protuberances is located at the free end of one of the arms and the second array of notches and/or protuberances is located at the free end of an opposite arm.

Preferably, the insert extends between the arms to limit relative rotation of the insert and plunger rod.

Typically, the free end of each of the four arms includes an array of notches and/or protuberances for, in use engaging with one of the four fingers.

Generally, the radial wall of the insert is a shell with the fingers extending radially inwards from one of its axial ends.

According to a second embodiment of the invention, the axial length of the second bore portion is greater than the axial length of the insert.

Typically, the axial end of the plunger rod opposite the plunger terminates in an enlarged head.

Generally, the enlarged head extends radially past the barrel.

Preferably, the enlarged head includes a head formation in the region where the enlarged head and plunger rod intersect, which head formation is sized and shaped in cross-section to correspond with the cross section of the second bore portion.

Typically, the head formation is in the form of a right circular cylinder.

Generally, the axial height of the head formation corresponds with the difference between the axial length of the second bore portion and the axial length of the insert.

Preferably, when the insert is fully inserted into the second bore portion, there is sufficient space in the second bore portion to receive the head formation therein.

Typically, the transition between the enlarged head and the head formation is tapered.

Generally, when the head formation is received within the second bore portion, the barrel and head formation form an effective seal against contaminants entering the second bore portion.

Preferably, the syringe further includes securing formations that lock the head formation within the second bore portion when the head formation and barrel are rotated relative to each other in one direction and release the head formation from the barrel when rotated relative to each other in the opposite direction.

Typically, the securing formations comprise:
(a) an L-shaped channel defined by: (i) the inner radial wall of the barrel in the vicinity of the second bore portion; and (ii) the outer radial surface of the head formation; and
(b) a protrusion extending either: (i) radially outwards from the head formation; or (ii) radially inwards from the barrel, respectively.

Generally, the enlarged head is threadably connectable to the plunger rod. Alternatively, it can be connected via a screw connector, a clip, a block slot, an interference fit, adhesive or weld.

Preferably, the inner radial wall of the barrel in the area of the first bore portion proximate the transition to the second bore portion includes a stopper that extending radially inwards.

Typically, the plunger rod includes a sealing formation proximal the enlarged head, the shape of which sealing formation is different in section orthogonal to the longitudinal axis of the plunger rod to the shape of the plunger rod in section orthogonal to the longitudinal axis of the plunger rod in the region including the notches and/or protuberances, so as substantially to cover the non-circular bore defined by the insert, when the plunger rod is in a depressed position in which the insert is proximal the enlarged head.

Generally, the plunger rod sealing formation, in section orthogonal to the longitudinal axis of the plunger rod, has a shape wherein four equally spaced arms radiate radially from the longitudinal axis of the plunger rod.

Preferably, each of the plunger rod sealing formation arms is slightly longer and wider than the plunger rod arms.

Typically, the free ends of each plunger rod sealing formation arm is linear.

Generally, the length of the plunger rod sealing formation arm(s) associated with the notches and/or protuberances on the plunger rod arm(s) is greater than the maximum radial height of the peaks of the notches and protuberances.

Preferably, the plunger rod sealing formation extends to and makes contact with the finger(s) on the insert when the plunger rod is in the depressed position.

Typically, the plunger rod sealing formation is sized and shaped to create an interference fit between the formations and the insert, when the plunger rod is in the depressed position.

Optionally, the enlarged head could include a tab protruding therefrom from the side opposite the side from which the plunger rod extends, and a frangible line at the point of intersection between the enlarged head and the tab.

Further optionally, the insert defines a slot along its radial wall, which slot extends between the axial ends of the insert.

There is also described a method of assembling a syringe described above, which method includes the steps of:
securing the plunger to the plunger rod (with the enlarged head removed therefrom) and inserting the plunger rod into the barrel, plunger first;
locating the insert over the end of the plunger rod distal the plunger and running the insert along the plunger rod until it is wholly received within the second bore portion of the barrel;
threadably connecting the enlarged head to the end of the plunger rod extending from the barrel (alternatively connecting the enlarged head to the end of the plunger rod via a screw connector, a clip, a block slot, an interference fit, adhesive or weld); and
depressing the plunger rod into the barrel until the head formation is received within the second bore portion of the barrel.

Typically, the method further includes the final step of rotating the plunger rod to lock the head formation within the second bore portion via the securing formations.

It will be appreciated that the plunger can alternatively be inserted into the barrel, followed by the plunger rod and that the two can be forced together within the barrel to connect them.

BRIEF DESCRIPTION OF THE DRAWINGS

The invention will now be described in more detail, by way of examples only, with reference to the accompanying drawings in which.

DESCRIPTIONS OF THE INVENTION

Figure 1:
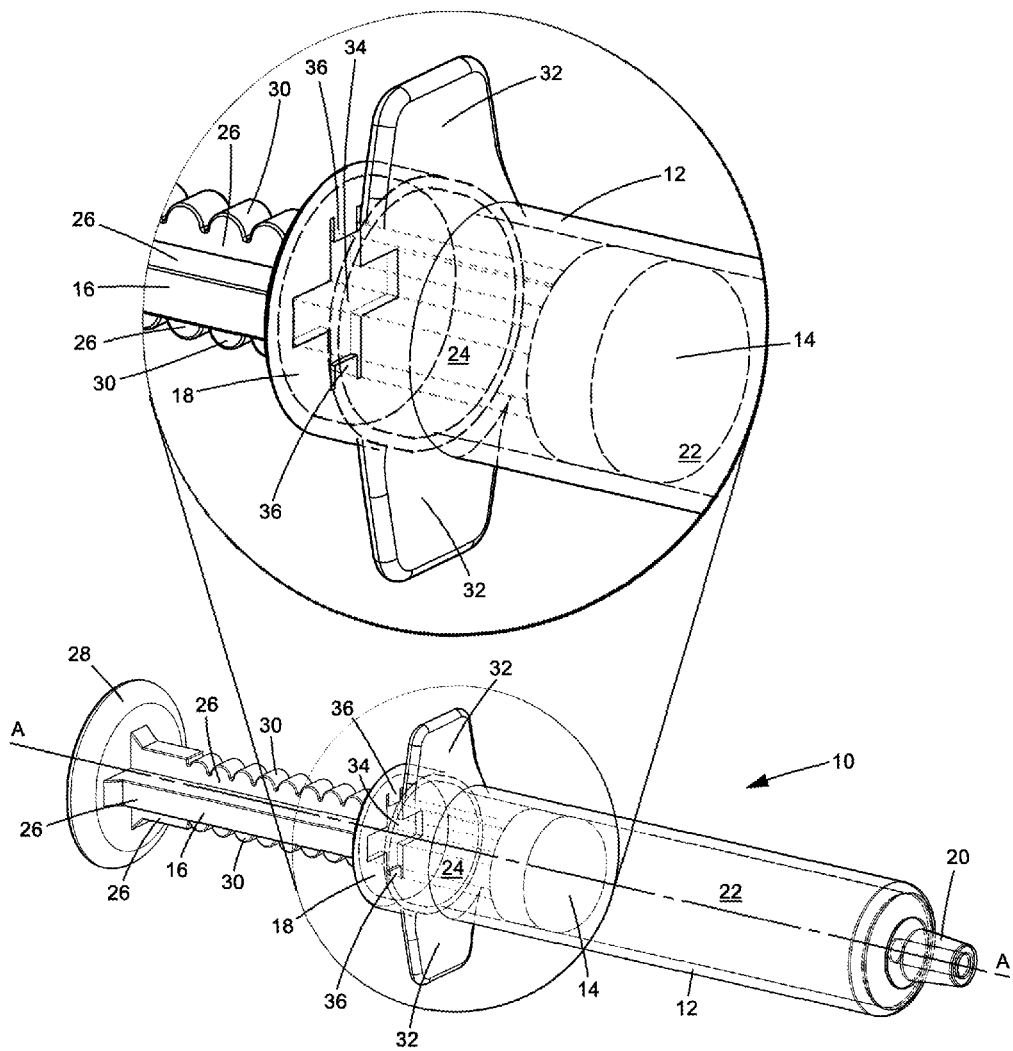
FIG. 1 is a perspective view of a syringe according to the invention according to a first embodiment of the invention.

With reference to FIGS. 1 to 4, a syringe 10 according to a first embodiment of the invention includes a barrel 12, a plunger 14, a plunger rod 16 and an insert 18.

Figure 2:
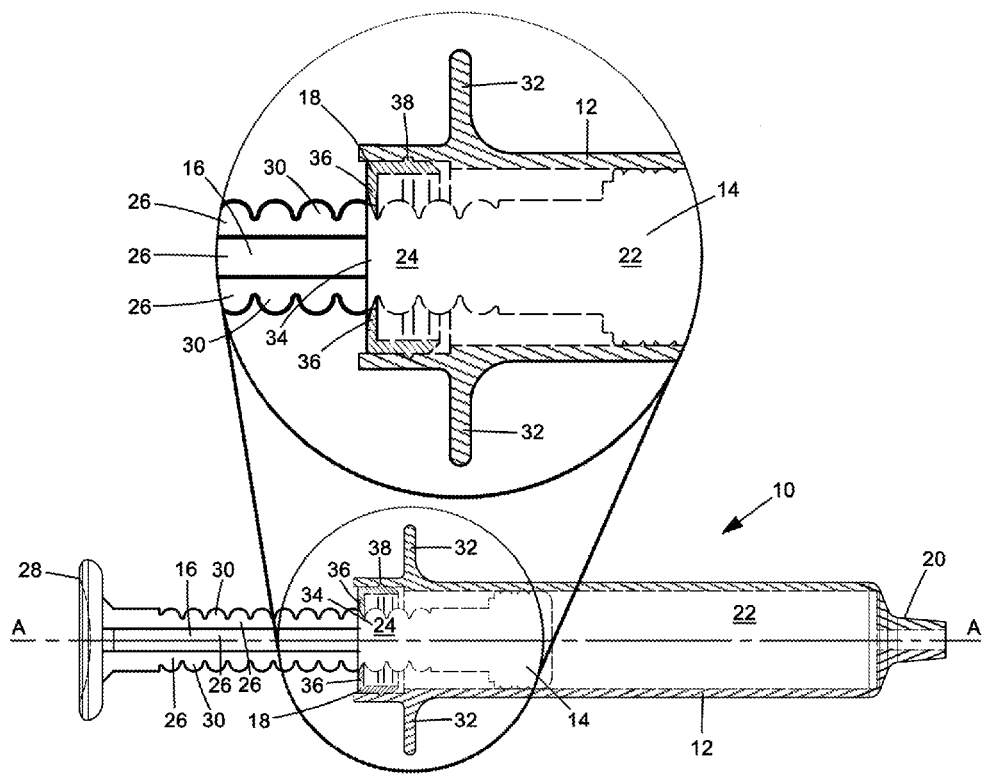
FIG. 2 is a cross sectional side view of the syringe in FIG. 1.
Figure 3:
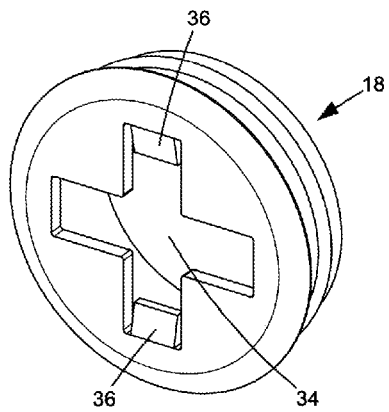
FIG. 3 is an upper perspective view of the insert forming part of the syringe in FIG. 1.
Figure 4:
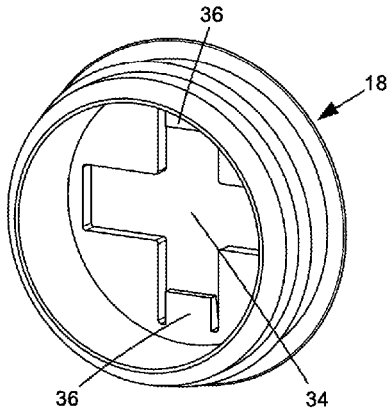
FIG. 4 is a lower perspective view of the insert in FIG. 3.

The barrel 12 is a monolithic body, being injection molded in one piece from a plastic material. The barrel 12 is right circular cylindrical, defining a longitudinal axis A-A. A first axial end of the barrel 12 terminates in a needle adapter 20 for connecting a needle (not shown) thereto. The barrel 12 is hollow, defining a bore that extends between its axial ends. The bore comprises: (i) a first bore portion 22 that is circular in cross section and extends from the needle adapter 20 partially towards the second axial end; and (ii) a second bore portion 24 that extends from the first bore portion 22 to the second axial end. At least a portion of the second bore portion 24 extends beyond the radius of the first bore portion 22. FIGS. 1 and 2 show the second bore portion having a circular cross section and the first and second bore portions 22 and 24 sharing a common longitudinal axis A-A. In other words, the second bore portion 24 is an extension of the first bore portion 22, but with a larger diameter.

A plunger 14 is located within the first bore portion 22 and movable therealong. The plunger 14 is circular in cross section and made from an elastomeric material. The diameter of the plunger 14 corresponds with the inner diameter of the barrel 12 in the vicinity of the first bore portion 22 to create a seal therebetween.

A plunger rod 16 extends from the plunger 14 towards the second axial end of the barrel 12, along the longitudinal axis A-A. The plunger rod 16, in section orthogonal to its longitudinal axis A-A, has a shape wherein four equally spaced arms 26 of the same length radiate from the longitudinal axis (i.e. in the shape of an "X"), and terminates in an enlarged head 28 in the shape of a disc.

The plunger rod 16 is movable between a retracted position shown in FIG. 1 in which the plunger 14 is proximal the insert 18 and a depressed position in which the enlarged head 28 is proximal the insert 18.

The free ends of two opposing arms 26 of the plunger rod 16 include arrays of notches and/or protuberances 30 extending along a portion of the length of the arms 16. It will be appreciated that although the plunger rod 16 has been shown with arrays of notches and/or protuberances 30 along two arms 26, an array of notches and/or protuberances 30 could alternatively be located on one arm 26 only or on three or four of the arms 26.

A pair of finger flanges 32 extends radially from the barrel 12. In use, a user's fore and index fingers (not shown) bear against the finger flanges 32 while the thumb (not shown) pushes the disc 28 on the plunger rod 16 towards the barrel 12.

FIGS. 1 and 2 show the transition of the first bore portion 22 to the second bore portion 24 in the region of the finger flanges 32.

Insert 18 is a right angled cylinder with an outer diameter and height corresponding to the inner diameter and length, respectively, of the second bore portion 24, such that the insert 18 is wholly located within the second bore portion 24 (i.e. does not protrude from the second axial end of the barrel 12). With specific reference to FIGS. 3 and 4, the insert defines a central non-circular bore 34 for receiving the plunger rod 16 therethrough. Fingers 36 extend into the insert bore 34 for, in use engaging with the notches and/or protuberances 30 on the plunger rod 16. The fingers 36 are symmetrically located at an axial end of the insert, i.e. each finger 36 is offset about the longitudinal axis A-A by 90 degrees.

Figure 9:
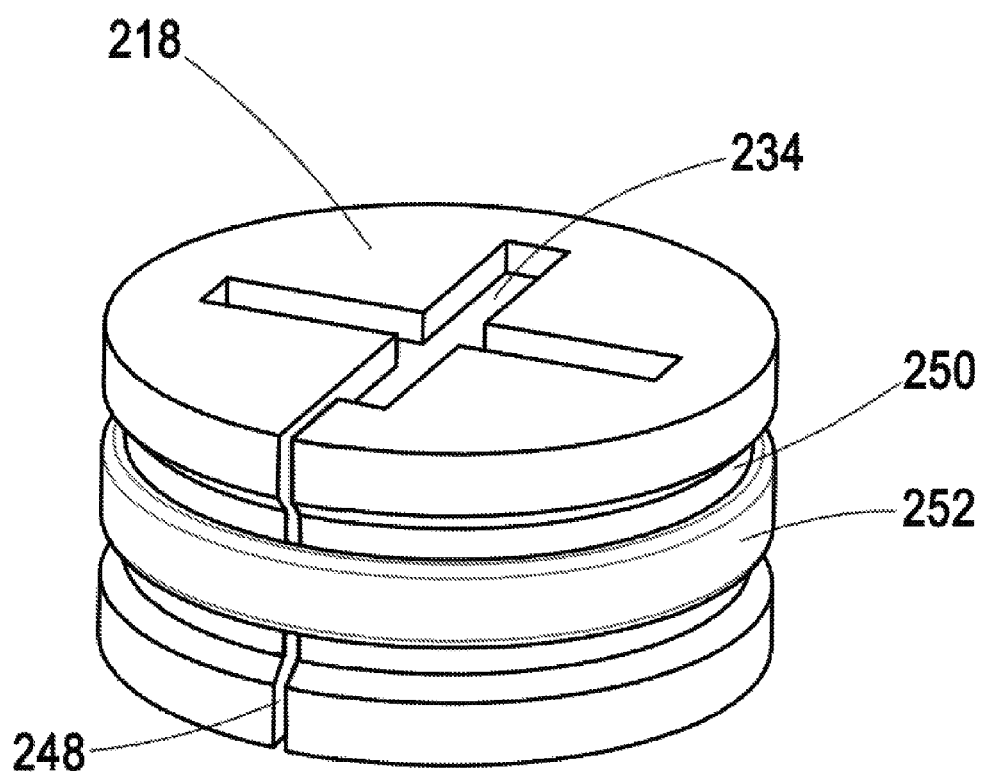
FIG. 9 is a perspective view of an insert according to a fourth embodiment of the invention.

Optionally, as shown in FIG. 9, the insert 218 could define a linear slot 248 along its radial wall, which slot 248 extends between the axial ends of the insert 218 (i.e. in the form of a C-clip). In such an arrangement, the plunger rod 16 could be received within the insert bore 234 via the slot 248 defined by the radial wall of the insert 218. The radial outer surface of the radial wall of the insert 218 could also define an annular groove 250 for receiving an elastomeric band 252 to prevent the insert 218 from splaying when the notches and/or protuberances 30 on the plunger rod 16 engage the fingers on the insert 218. The elastomeric band 252 could be sized to fit the internal diameter of the second bore portion 24 of the barrel 12.

The radial wall of the insert 18 is a shell. An axial end of the insert 18 (opposite the end defining the bore 34) could be tapered (not shown) to facilitate insertion of the insert 18 into the second portion 24 of the barrel 12.

Referring back to FIGS. 1 and 2, the insert 18 is shaped to extend at least partially between the plunger rod 16 arms 26 so as to limit relative rotation of the plunger rod 16 and insert 18.

Furthermore, the insert includes a notch 38 that co-operates with a corresponding protuberance 38 that extends radially inwards from the barrel to secure the insert 18 within the second bore portion 24. Alternatively, it will be appreciated that: (i) the insert 18 could include a protuberance while the barrel 12 defines a corresponding notch; (ii) the insert 18 could be adhered to the barrel 12; or (iii) an interference fit between the insert 18 and barrel 12 could secure the insert 18 within the second bore portion 24.

In use, with the insert 18 located within the second bore portion 24 and the plunger rod 16 threaded through the bore 34 defined by the insert 18, when the plunger rod 16 is moved relative to the barrel 12 along axis A-A, two fingers 36 on the insert 18 run along the notches and/or protuberances 30 on the plunger rod 16 to generate audible clicks.

Preferably, the fingers 36 are sufficiently thin and flexible to generate audible clicks without materially resisting movement of the plunger rod 16 relative to the barrel 12. The audible clicks assist the doctor to administer the correct dosage to the patient, and satisfy the patient that the dosage requested/prescribed has been administered. Furthermore, the fingers 36 provide some resistance against movement of the plunger rod 16 along the barrel 12. As such, a user can draw the plunger 14 along the barrel 12 (i.e. away from the needle adaptor 20) to a predetermined position and release the plunger rod 16 to allow the vacuum generated by such draw to fill the barrel 12 with medicament. The resistance inhibits the vacuum from causing the plunger 14 to move partially back towards the needle adaptor 20 while the medicament is being drawn.

Furthermore, to indicate whether a syringe 10 has been used, the enlarged head 28 could include a tab (not shown) that extends from its planar surface (i.e. the surface to which a user would apply pressure to depress the plunger rod 16 within the barrel 12) with a frangible line at the point of intersection between the tab and enlarged head 28 to facilitate easy removal of the tab from the enlarged head 28 by the user prior to use.

Figure 5:
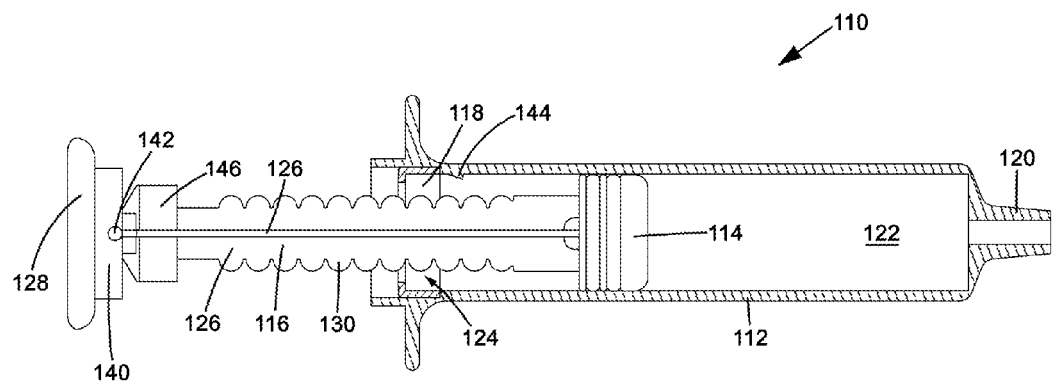
FIG. 5 is a side view of a syringe according to a second embodiment of the invention.
Figure 6:
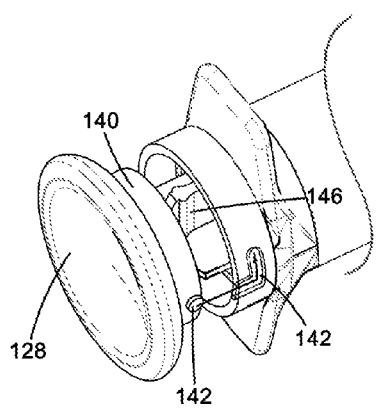
FIG. 6 is a perspective view of the syringe in FIG. 5.
Figure 7:
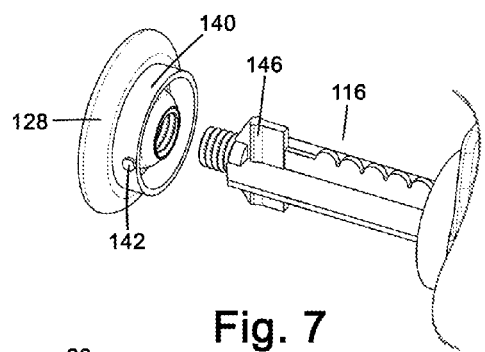
FIG. 7 is a perspective view of the syringe in FIG. 5 with the head unthreaded from the plunger rod.

A second embodiment of a syringe 110 according to the invention is shown in FIGS. 5 to 7. The syringe 110 according to the second embodiment of the invention is substantially similar to the syringe 10 according to the first embodiment shown in FIGS. 1 to 4. The main differences being that:

(i) the axial length of the second bore portion 124 is greater than the axial length of the insert 118; and (ii) the enlarged head 128 on the plunger rod 116 includes a head formation 140 where the enlarged head 128 and plunger rod 116 intersect, which head formation 140 is sized and shaped in cross-section to correspond with the cross section of the second bore portion 124. FIGS. 5 to 7 show the head formation 140 in the form of a right circular cylinder.

More specifically, the axial height of the head formation 140 corresponds with the difference between the axial length of the second bore portion 124 and the axial length of the insert 118. Such that, when the insert 118 is fully inserted into the second bore portion 124, there is sufficient space in the second bore portion 124 to receive the head formation 140 therein. Since the head formation 140 fits snugly within the barrel 112 in the vicinity of the second bore portion 124, the barrel 112 and head formation 140 form an effective partial seal against contaminants entering the second bore portion 124.

Turning specifically to FIG. 6, furthermore, the head formation 140 and barrel 112 in the vicinity of the second bore portion 124 includes co-operating securing formations 142 that lock the head formation 140 within the second bore portion 124 when the head formation 140 and barrel 112 are rotated relative to each other in one direction and release the head formation 140 from the barrel 112 when rotated relative to each other in the opposite direction. The securing formations 142 comprise an L-shaped channel defined by the inner radial wall of the barrel 112 in the vicinity of the second bore portion 124 and a protrusion extending radially from the head formation 140, which protrusion is sized and shaped to be received within and run along the channel. Alternatively, the protrusion could extend radially inwards from the barrel 112 and the head formation 140 could define the channel on its radial outer surface. The securing formations 142 are useful to indicate to a user whether the syringe 110 has previously been used (i.e. whether it is sterile).

The syringe 110 could also include a biasing means (not shown) that biases the enlarged head 128 from the barrel 112/insert 118 when in the depressed position. With this arrangement, when the securing formations 142 do not lock the head formation 140 within the second portion 124 of the barrel 112, the biasing means will cause the head formation 140 to exit the second portion 124 of the barrel 112. This will indicate to a user that the syringe 110 has previously been used.

The enlarged head 128 extends radially beyond the outer perimeter of the end of the barrel 112 so as to enable a user to grip the enlarged head 128 and rotate it while the head formation 140 is housed within the second bore portion 124 of the barrel 112. The transition between the enlarged head 128 and the head formation 140 could be tapered (not shown) to facilitate a seal between the head formation 140 and the barrel 112 in the area of the second bore portion 124.

To facilitate assembly of the syringe 110, the enlarged head 128 is threadably connected to the plunger rod 116 (as shown in FIG. 7). To assembly the syringe 110 (alternatively, the enlarged head 128 and plunger rod 116 can be connected via a screw connector, a clip, a block slot, an interference fit, adhesive or weld):
  the plunger 114 is secured to the plunger rod 116 (with the enlarged head 128 removed therefrom) and inserted into the barrel 112, plunger 114 first;
  the insert 118 is located over the end of the plunger rod 116 distal the plunger 114 and threaded/run along the plunger rod 116 until it is wholly received within the second bore portion 124 of the barrel 112;
  the enlarged head 128 is threadably connected to the end of the plunger rod 116 extending from the barrel 112;
  the plunger rod 116 is depressed into the barrel 112 until the head formation 140 is received within the second bore portion 124 of the barrel 112;
  the plunger rod 116 is rotated to lock the head formation 140 within the second bore portion 124 via the securing formations 142.

It will be appreciated that the plunger 114 can alternatively be inserted into the barrel 112, followed by the plunger rod 116 and that the two can be forced together within the barrel 112 to connect them.

The inner radial wall of the barrel 112 in the area of the first bore portion 122 proximate the transition to the second bore portion 124 includes a stopper 144 that extending radially inwards. The stopper 144 is wedge-shaped at one end only so as to permit the plunger 114 to be inserted into the first bore portion 122 of the barrel 112 by riding up the wedge and over the stopper 144. Once past the stopper 144, the plunger 114 may freely travel along the first bore portion 122 towards the needle adapter 120. However, when the plunger 114 is retracted from the barrel 112, i.e. away from the needle adapter 120, movement of the plunger 114 along the barrel 112 is limited by the stopper 144. By limiting retraction of the plunger 114 from the barrel 112, a user can safely retract the plunger 114 further along the barrel 112 than would otherwise be the case. As, without the stopper 144, there is a risk that a user may pull the plunger 114 too far along the barrel 112 and out of the first bore portion 122, adversely impacting sterility of the syringe 110.

The head formation 140 could similarly be incorporated into the syringe described in ZA2013/1882.

Turning back to FIG. 5, a plunger rod sealing formation 146 may extend axially from the head formation 140. The shape of the plunger rod sealing formation 146 is different in section orthogonal to the longitudinal axis of the plunger rod 116 to the shape of the plunger rod 116 in section orthogonal to the longitudinal axis of the plunger rod in the region including the notches and/or protuberances 130, so as substantially to cover the non-circular bore 134 defined by the insert 118 (i.e. the aperture defined by the insert 118 and fingers (shown as 36 in FIGS. 1,3 and 4) when the plunger rod 116 is in the depressed position (i.e. when the insert 130 is proximal the enlarged head 128).

The cross-sectional area of the plunger rod sealing formation 146 is greater than the cross-sectional area of the plunger rod 116 in the vicinity of the notches and/or protuberances 130. The plunger rod sealing formation 146 comprises four equally spaced arms radiating from the longitudinal axis of the plunger rod 116 (i.e. in the shape of an "X"). At least two arms of the plunger rod sealing formation 146 are slightly (radially) longer and wider than the plunger rod arms 126. And, whereas at least one plunger rod arm 126 includes notches and/or protuberances 130, the corresponding free end (i.e. radial outer end) of the sealing formation arm 146 is linear (i.e. it does not include such notches and protuberances and is of consistent length (measured radially from the longitudinal axis of the plunger rod 116)). The length of such plunger rod sealing formation arm 146 at least corresponds to the maximum radial height of the peaks of the notches and/or protuberances 130. Preferably, the radial length of the plunger rod sealing formation arm 146 associated with the notches and/or protuberances 130 is slightly greater than the radial height of the peaks of the notches and protuberances 130.

It will be appreciated that the height of the plunger rod sealing formation arms 146 could increase along its length from the plunger 114 to the enlarged head 128. Alternatively, the plunger rod 116 could include a transition portion that gradually transitions along its axial length from the shape of the plunger rod arms 126 to the shape of the plunger rod sealing formation 146.

It will also be appreciated that, due to the shape of the plunger rod sealing formation 146, the gap(s) between the insert 118 and plunger rod 116 is less when the plunger rod 116 is in the depressed position with the plunger rod sealing formation 146 located within the bore 134 defined by the insert 118 than when the plunger rod is extended from the depressed position with the arms 126 of the plunger rod 116 (with notches and/or protuberances 130) located within the bore 134 defined by the insert 118. By reducing the gap between the plunger rod 116 and insert 118/substantially covering the non-circular bore 134 defined by the insert 118, the plunger rod sealing formation 146 provides a better seal between the plunger rod 116 and insert 118 when the plunger rod 116 is in the depressed position.

Figure 8:
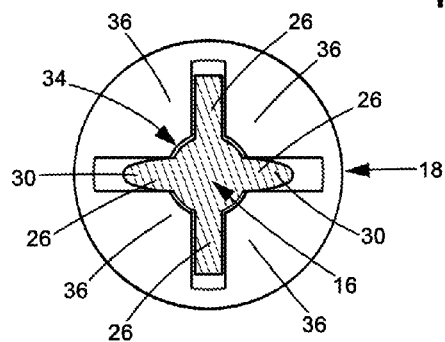
FIG. 8 is a plan view of an insert according to a third embodiment of the invention with the plunger rod located therein.

FIG. 8 shows a third embodiment of the insert 18, which defines a bore 34 and having fingers 36. The plunger rod 12 includes arms 26, two of which include notches and/or protuberances 30 that engage with the fingers 36. In this arrangement, two fingers 36 engage with the notches and/or protuberances 30 on an arm 26. Since a total of four fingers 36 engage with the notches and/or protuberances 30, the audibility of each click is increased.

It will be appreciated the plunger 14 can be connected to the plunger rod 16 in various ways, including via a screw connector, a clip, a block slot, an interference fit, adhesive and weld. This enables the plunger rod 16 to be substituted with rods of varying lengths. In addition, the plunger rod 16 can be modular with the modular parts being connected using any of the aforementioned connectors, so as to adjust the length of the plunger rod 16.

It will also be appreciated that, although the plunger rod 16 has been illustrated with notches and/or protuberances along a free end of opposing plunger rod 16 arms 26, such formations could alternatively be located at the point of intersection of the plunger rod 16 arms 26, i.e. near the axis of the plunger rod 16.

The invention claimed is:

1. A syringe including:
a monolithic barrel defining a longitudinal axis, first and second axial ends, and a bore extending along the longitudinal axis, the bore terminating in a needle adapter at the first axial end and being divided into two bore portions, a first bore portion having a first axial length extending from the needle adapter partially towards the second axial end and a second bore portion having a second axial length extending from the first bore portion to the second axial end, wherein the first bore portion is circular in cross section and the second bore portion has a cross sectional shape that at least partially extends beyond the radius of the first bore portion;
at least one finger flange extending from the monolithic barrel;
a plunger sized to fit within and move along the longitudinal axis of the first bore portion, with the plunger sealed against an inner wall of the monolithic barrel within a region of the first bore portion;
a plunger rod extending along the longitudinal axis of the monolithic barrel towards the second axial end, and terminating opposite from the plunger in an enlarged head that extends radially past the monolithic barrel and includes a head formation in a region where the enlarged head and the plunger rod intersect, the head formation being sized and shaped in cross-section to correspond with the cross sectional shape of the second bore portion, the head formation being in the form of a right circular cylinder, a transition between the enlarged head and the head formation being tapered, the plunger rod including a first array of at least one of notches and protuberances along at least a portion of its length, and further including a sealing formation proximal to the enlarged head, the shape of which sealing formation being different in section orthogonal to the longitudinal axis of the plunger rod to the shape of the plunger rod in section orthogonal to the longitudinal axis of the plunger rod in the region including the at least one of notches and protuberances, the plunger rod sealing formation, in section orthogonal to the longitudinal axis of the plunger rod, has a shape wherein four equally spaced arms radiate radially from the longitudinal axis of the plunger rod, each of the plunger rod sealing formation arms being slightly longer and wider than the plunger rod arms, free ends of each plunger rod sealing formation arm being linear, a length of at least one of the plunger rod sealing formation arms associated with the at least one of notches and protuberances on the at least one plunger rod arms being greater than a maximum radial height of a peak of the at least one of notches and protuberances; and
an insert having a third axial length that is less than the second axial length, and being sized to fit wholly within the second bore portion such that when the insert is fully inserted into the second bore portion, there is sufficient space in the second bore portion to receive the head formation therein, an axial height of the head formation corresponding with a difference between the second axial length and the third axial length, the insert defining a non-circular bore through which the plunger rod extends and including a first finger extending into the bore defined by the insert for, in use, engaging the first array of at least one of notches and protuberances on the plunger rod, wherein, when the plunger rod is in a depressed position with the head formation received within the second bore portion, an interference fit through direct contact between the enlarged head and the barrel creates an effective seal against entry of contaminants into the second bore portion of the barrel, and an interference fit is established between the plunger rod sealing formation and the insert, the plunger rod sealing formation being shaped so as substantially to cover the bore defined by the insert, the plunger rod sealing formation being shaped so as substantially to cover the bore defined by the insert when the plunger rod is in a depressed position in which the insert is proximal to the enlarged head.

2. A syringe according to claim 1, wherein:
the plunger rod includes a second array of at least one of notches and protuberances extending from a side of the plunger rod opposite the side on which the first array of at least one of notches and protuberances are located; and
the insert includes a second finger arranged opposite the first finger, which second finger extends into the bore defined by the insert and, in use, engages the second array of at least one of notches and protuberances.

3. A syringe according to claim 2, wherein:
the second bore portion has a diameter greater than the first bore portion;
the first and second bore portions share a common longitudinal axis; and
the first bore portion extends from the needle adapter to the at least one finger flange and the second bore portion extends from the first bore portion to the second axial end of the barrel.

4. A syringe according to claim 3, wherein:
the insert is right circular cylindrical with a diameter corresponding to the diameter of the second bore portion; and
the axial height of the insert substantially corresponds with the length of the second bore portion, such that the insert does not protrude from the second axial end of the barrel.

5. A syringe according to claim 4, wherein:
the insert is secured to the barrel within the second bore portion by an interference fit between the insert and barrel; and
the insert includes third and fourth fingers, wherein the first, second, third and fourth fingers are symmetrically arranged around the bore defined by the insert.

6. A syringe according to claim 5, wherein:
the plunger rod, in section orthogonal to its longitudinal axis, has a shape wherein four equally spaced arms of the same length radiate radially from the longitudinal axis; and
the first array of at least one of notches and protuberances is located at a free radially outer end of one of the arms and the second array of at least one of notches and protuberances is located at a free radially outer end of an opposite arm.

7. A syringe according to claim 6, wherein the insert extends between the arms to limit relative rotation of the insert and plunger rod.

8. A syringe according to claim 7, wherein the free end of each of the four arms includes an array of at least one of notches and protuberances for, in use engaging with one of the four fingers.

9. A syringe according to claim 8, wherein the radial wall of the insert is a shell with the fingers extending radially inwards from one of its axial ends.

10. A syringe according to claim 1, wherein:
  the insert defines a slot along its radial wall, which slot extends between the axial ends of the insert;
  the radial wall of the insert defines an annular groove for receiving an elastomeric band to prevent the insert from splaying when the at least one of notches and protuberances on the plunger rod engage the fingers on the insert; and
  the elastomeric band is sized to fit the internal diameter of the second bore portion of the barrel.

* * * * *